United States Patent [19]

Kaufman

[11] Patent Number: 5,284,621
[45] Date of Patent: Feb. 8, 1994

[54] WASTE FLUID DISPOSAL AID

[76] Inventor: Jack W. Kaufman, 357 Frankel Blvd., Merrick, N.Y. 11566

[21] Appl. No.: 943,119

[22] Filed: Sep. 10, 1992

Related U.S. Application Data

[63] Continuation of Ser. No. 215,370, Jul. 5, 1988, abandoned, Continuation-in-part of Ser. No. 105,875, Oct. 7, 1987, abandoned.

[51] Int. Cl.$^5$ .............................................. A61L 9/00
[52] U.S. Cl. .................................. 422/32; 206/524.6; 206/524.7; 210/751; 220/521; 220/908; 422/28
[58] Field of Search ............................ 422/28, 30, 32; 206/219–221, 568, 524.6, 524.7; 220/521, 908; 604/27, 54–55, 333, 349, 350, 335; 128/760; 210/751, 749; 428/35.7

[56] References Cited

U.S. PATENT DOCUMENTS

| | | | |
|---|---|---|---|
| 3,190,373 | 6/1965 | Weathersby | 206/524.7 |
| 3,347,410 | 10/1967 | Schwartzman | 206/222 X |
| 3,603,469 | 9/1971 | Magni | 206/222 |
| 3,715,189 | 2/1973 | Nighohossian et al. | 206/222 X |
| 3,809,224 | 5/1974 | Greenwood | 206/219 |
| 3,870,147 | 3/1975 | Orth | 206/222 |
| 3,968,872 | 7/1976 | Cavazza | 206/222 |
| 4,193,698 | 3/1980 | Gartner | 206/219 X |
| 4,314,558 | 2/1982 | Korpman | 128/283 |
| 4,315,570 | 2/1982 | Silver et al. | 206/221 |
| 4,417,892 | 11/1983 | Meisch | 604/323 |
| 4,516,884 | 5/1985 | Douty | 206/219 X |
| 4,518,507 | 5/1985 | Conner | 210/747 |
| 4,550,825 | 11/1985 | Sutryn et al. | 206/222 |
| 4,615,810 | 10/1986 | Conner | 210/751 |
| 4,748,069 | 5/1988 | Cullen | 206/524.7 X |
| 4,749,600 | 6/1988 | Cullen et al. | 206/524.7 X |
| 4,853,266 | 8/1989 | Cullen | 206/524.7 X |
| 4,856,651 | 8/1989 | Francis, Jr. | 206/219 |

Primary Examiner—Robert J. Warden
Assistant Examiner—Amalia Santiago
Attorney, Agent, or Firm—Lackenbach Siegel Marzullo Aronson & Greenspan

[57] ABSTRACT

A medical waste fluid kit for preparing for disposal waste fluid collected from a patient comprising a substantially rigid, fixed shaped vessel having and being closed by a rigid cap having waste fluid inlet for introducing a waste fluid into said vessel and an outlet extending from and through the rigid cap; a composition comprising at least one hydrophilic xerogel in the form of a powder which includes at least one water-insoluble hydrophilic polymer for immobilizing the waste fluid; a container, having a surface area containing the hydrophilic xerogel for placement in the vessel for disposal of the waste fluid collected therein, and the surface area of the container comprising a material which breaks up when brought into contact with the waste fluid for releasing the hydrophilic xerogel into the vessel for admixing with the waste fluid, thereby immobilizing and solidifying same within the vessel and minimizing the hazards of handling the waste fluid which may be infectious.

17 Claims, 8 Drawing Sheets

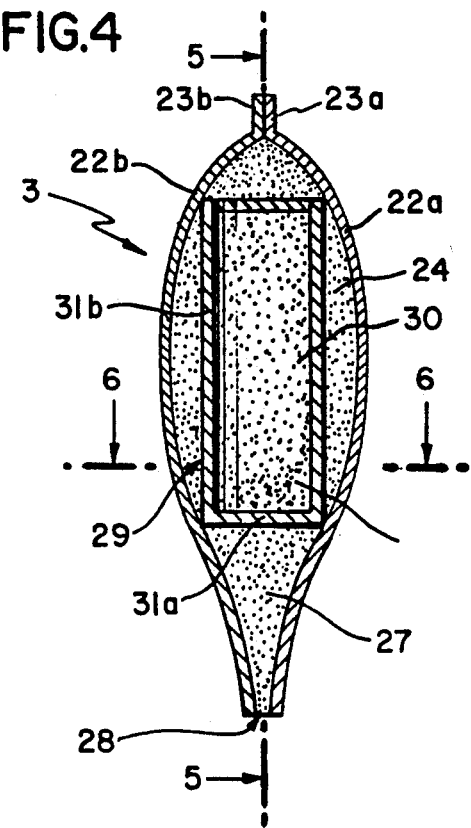
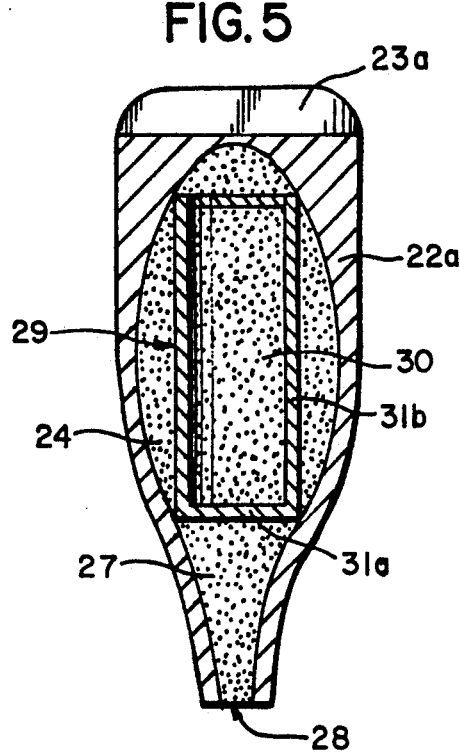
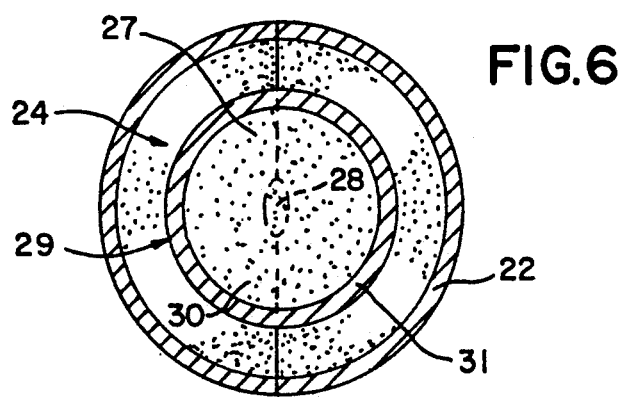

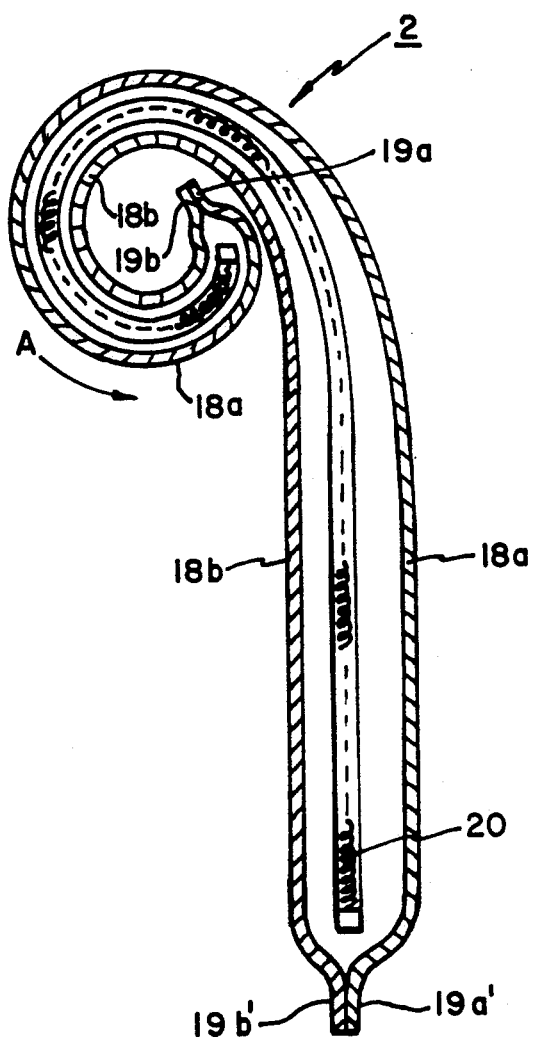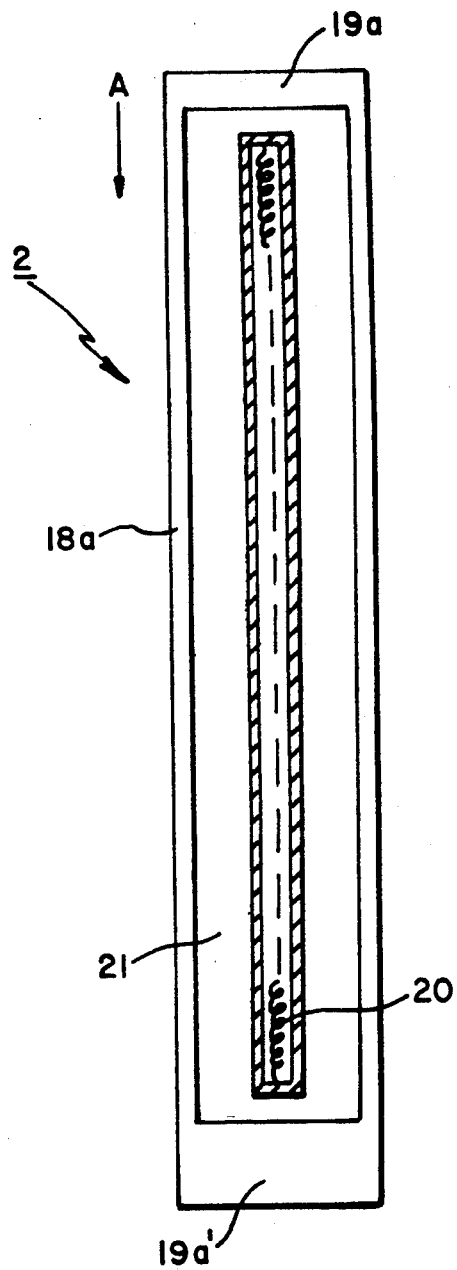
FIG.13
FIG.12

WASTE FLUID DISPOSAL AID

This application is a continuation of U.S. application Ser. No. 07/215,370 filed Jul. 5, 1989 (now abandoned), which is a continuation-in-part of my co-pending application Ser. No. 105,875 filed Oct. 7, 1987 (now abandoned).

BACKGROUND OF THE INVENTION

This invention relates to the safe disposal of aqueous fluid waste materials. More particularly, it relates to a composition for use in the disposal of aqueous waste fluids such as blood, drained from body cavities of patients pre- and post-operatively as well as during operations, said composition comprising at least one hydrophilic xerogel comprising at least one hydrophilic water-insoluble polymer. If desired, said composition further comprises materials for disinfecting said fluids.

The invention also relates to a method for preparing said fluids for disposal which comprises the addition of said composition to said fluids whereby the xerogel portion of the composition absorbs the aqueous portion of the fluids resulting in on insoluble gel in which the remainder of said fluids is absorbed and immobilized. The disinfectant, if present, destroys or, at least, deactivates infectious agents within said fluids. Thus, the immobilized waste materials are then disposed of by known methods.

The invention further relates to articles comprising containers for use in said disposal wherein said containers are placed within vessels for, and prior to commencement of, the collection of said fluids to provide for addition of the composition of the invention thereto without necessitating opening of the vessel with it concomitant risk of releasing undesirable materials contained in the fluids to the atmosphere. In the event the disinfectant and xerogel are interactive, or it is desired to effect interaction of the fluids therewith, consecutively, said containers may comprise two compartments separated from each other to allow for admixture of the components prior to addition to the fluids or for consecutive addition thereto.

Aqueous fluid waster materials, such as blood, are often drained from body cavities, such as pleurae, before, during and after surgery, for disposal. The drained fluids, which usually comprise harmful components, are collected in vessels which are sealed and discarded or emptied into sinks or toilet bowls.

Furthermore, during sealing and removing said vessels from the patient a portion of the collected fluids may escape from the vessel and contact the surrounding area and personnel proximal thereto.

If the fluids comprise infectious components, e.g., hepatitis B virus, there is also a risk of said fluids infecting said personnel and others who might subsequently come in contact with the spilled fluids.

The potential problems and risks have been reported upon by Mary M. Maijer, BN, RN in the article "Emptying and Disposing of wound Drainage ... An infection Hazard" (in Today's OR Nurse, 9 (11), 11-16, (1987)).

Thus, post-surgical wound infection has many serious implications for society. For instance, hospital stays are increasing at an average of 3.8 to 10.1 days at a cost, for hospitalization alone, on the order of $2000. Other cost are accounted for by extra personnel required, lost employment, etc. the resultant average economic loss has been estimated to be on the order of about 9.5 billion dollars.

Many of these costs are not paid for by third parties (e.g., insurance companies and Medicare) and must be borne by the healthcare institutions themselves. Furthermore, said institutions and physicians have been subjected to an increasing number of liability suits as a result of these incidents.

One of the more significant factors influencing the incidence of such infections is the availability of means for the transfer of the infecting microorganisms.

A leading means of such transfer has been found to be carriage by healthcare personnel, such as transfer of Pseudonomas on the hand of nursing personnel.

It has been suggested that a transfer of methicillin resistant S. aureous among large medical schools and their affiliated hospitals has been effected though the patient—in house staff circuit, and the organisms for this and other infections can be found in wounds, blood and other body fluids.

It is now being recognized that healthcare personnel themselves are at increasing risk of acquiring infections from their patients by contact with such contaminated body fluids.

Thus, such personnel have acquired hepatitis B virus (HBV), AIDS and Human Immunodeficiency Virus (HIV) by exposure to the blood of patients having these diseases.

The common factor statistically associated with the acquisition of the diseases has more often been contact of the skin and clothing with blood, and other body fluids rather than accidental needle sticks, swallowing specimens or failing to wash hands and wear gloves frequently.

Thus, of six cases of AIDS infection in healthcare workers, with no know risk factors, two only had extensive contact with blood while three workers acquired HIV following non needle exposure to the blood from infected patients where the blood had either spilled or splattered on their skin or mucous membranes. In one instance the worker wore protective gloves.

An increasing prevalence of HIV has increased the potential for such exposures.

In view of the above elimination or, least, minimalization of healthcare workers exposure to such contaminated fluids must be achieved.

Major sources of such exposures are closed wound drainage devices which require frequent handling and manipulation.

Splashing and aerosolization during handling and emptying the devices, often into sinks and toilet bowls, as well as the usual practices of disposing thereof cause an increased level of infectious materials on the hands and other body parts.

For instance, in collection canisters who covers must be removed for emptying thereof the undersides of the covers as well as the lips of the canisters are covered with contaminants and the fluids may splash as the covers are snapped on and off.

Furthermore, release of the aerosolized components of the fluids contained within the canister create another hazard to the healthcare workers.

While measures are available for reducing the above factors, with a greater or lesser efficacy, it is desirable that the source of the hazards, i.e., escape of the contaminants from the canister, be eliminated and if such escape occurs the infectious character of the fluids eliminated or, at least, minimized.

Therefore, it is necessary that the closed vessels remain sealed during the handling processes.

The Surgidyne Saber and 3C System has been proposed for retaining and disposing of the body fluids without opening the collection vessel.

However, this system retains the drained fluids in their highly mobile and infectious state. Where the canister to open accidentally, e.g., by bursting upon impact the fluids would spill and perhaps splatter therefrom and aerosolization might occur thereby, again, giving rise to the problems the system was eliminate.

Furthermore, at any time during the disposal procedure, e.g., while placing vessels in canisters and transporting the canisters to disposal sites, the vessels might break open spewing their contents on, and possibly infecting, their surroundings including personnel in the proximity thereof.

It has now been found that the above problems may be obviated by use of the compositions of the instant invention in accordance with the methods and in conjunction with the articles thereof.

SUMMARY

It is an object of the invention to provide a composition for use in the safe disposal of aqueous waste fluids which converts said fluids into a non-fluid form.

It is another object of the invention to provide a composition as described above comprising at least one hydrophilic xerogel comprising at least one water-insoluble hydrophilic polymer.

Another object of the invention is to provide a composition as described above further comprising at least one disinfecting component selected from the group comprising germicides and germistats, such as bactericides, bacteriostats, fungicides, fungistats, and the like.

Yet another object of the invention is to provide a composition as described above wherein said composition is used in the form of a free-flowing powder further comprising a suitable carrier.

Another object of the invention is to provide a composition as described above wherein the components thereof are coated with a composition which will slowly dissolve upon contact with said waste fluids thereby gradually releasing the components of said composition to interact with the waste fluid.

Still another object of the invention is to provide a composition as described above in the form of a compacted article which will disintegrate upon contact with said aqueous fluid waste material thereby gradually releasing the components of said composition to interact with the waste fluid.

Another object of the invention is to provide a composition as described above wherein said article comprises a compacted mixture comprising said xerogel, and, if present, said disinfectant, said article being coated with a composition which will slowly dissolve upon contact with said waste fluids thereby gradually releasing the components of said composition to interact with the waste fluids.

Yet another object of the invention is to provide a composition as described above wherein said xerogel and disinfectant are separate until, and mixed, just prior to addition of said composition to said waste fluids.

Another object of the invention is to provide a composition as described above wherein said components are added to said waste fluids consecutively.

Yet another object of the invention is to provide a method for rendering aqueous fluid waste materials safe for disposal which comprises adding a composition as described above to said fluids, effecting essentially complete mixing of the fluids and composition whereby the resultant mixture becomes gelled or solidifies and then disposing of said gelled or solidified mixture.

Another object of the invention is to provide a method as described above wherein said composition further comprises a disinfectant to destroy pathogens within said waste fluids.

Still another object of the invention is to provide a method as described above wherein said xerogel and disinfectant are separated from each other until, and then mixed, just prior to addition to said waste fluids.

Yet another object of the invention is to provide a method as described above wherein said xerogel and said disinfectant are added to said waste fluids consecutively with the disinfectant being added first to destroy any pathogens present before gelation.

Another object of the invention is to provide an article for use in the safe disposal of waste fluids collected in a closed collection vessel with said article comprising a sealed envelope, to contain said composition, and openable without opening said vessel.

Yet another object of the invention is to provide a method for rendering non-gaseous waste fluids safe for disposal which comprises adding a composition as described above to said fluids, effecting essentially complete mixing of the fluids and composition, whereby the resultant mixture becomes gelled or solidifies and then disposing of said gelled or solidified mixture.

According to another object of the invention there is provided an article comprising a sealed chamber to contain the components of said composition; the article to be emplaced within the collection vessel before addition of the waste fluids thereto with said article to be opened, after the vessel has been sealed and collection of the fluids commenced, to release its contents thereto to interact with said fluids.

Another object of the invention is to provide an article as described above wherein said compartments are isolated from each other whereby consecutive additions, of the contents thereof, to the waste fluids is permitted.

Yet another object of the invention is to provide an article, as described above, wherein said compartments comprise chambers within said vessels with said chambers further comprising means for opening thereof to effectuate release of their contents to the vessel.

These and other objects of the invention will be in part discussed and in part apparent upon consideration of the detailed description of the preferred embodiment and the attached drawings.

DETAILED DESCRIPTION OF THE DRAWINGS

FIG. 4 is a sectional view of an article to be used in conjunction with said embodiment.

FIG. 5 is a sectional view of the article shown in FIG. 4, and taken along the line 5—5 of FIG. 4.

FIG. 6 is a bottom plan view of the article shown in FIG. 4, and taken along the line 6—6 of FIG. 4.

FIG. 12 is a front view, party in section of a further modification of an article of the invention, similar to that of FIG. 2.

FIG. 13 is a partial sectional view of the article of FIG. 12, and shown being prepared for use in the practice of the invention.

DETAILED DESCRIPTION OF THE PREFERRED EMBODIMENT

Figure 1:
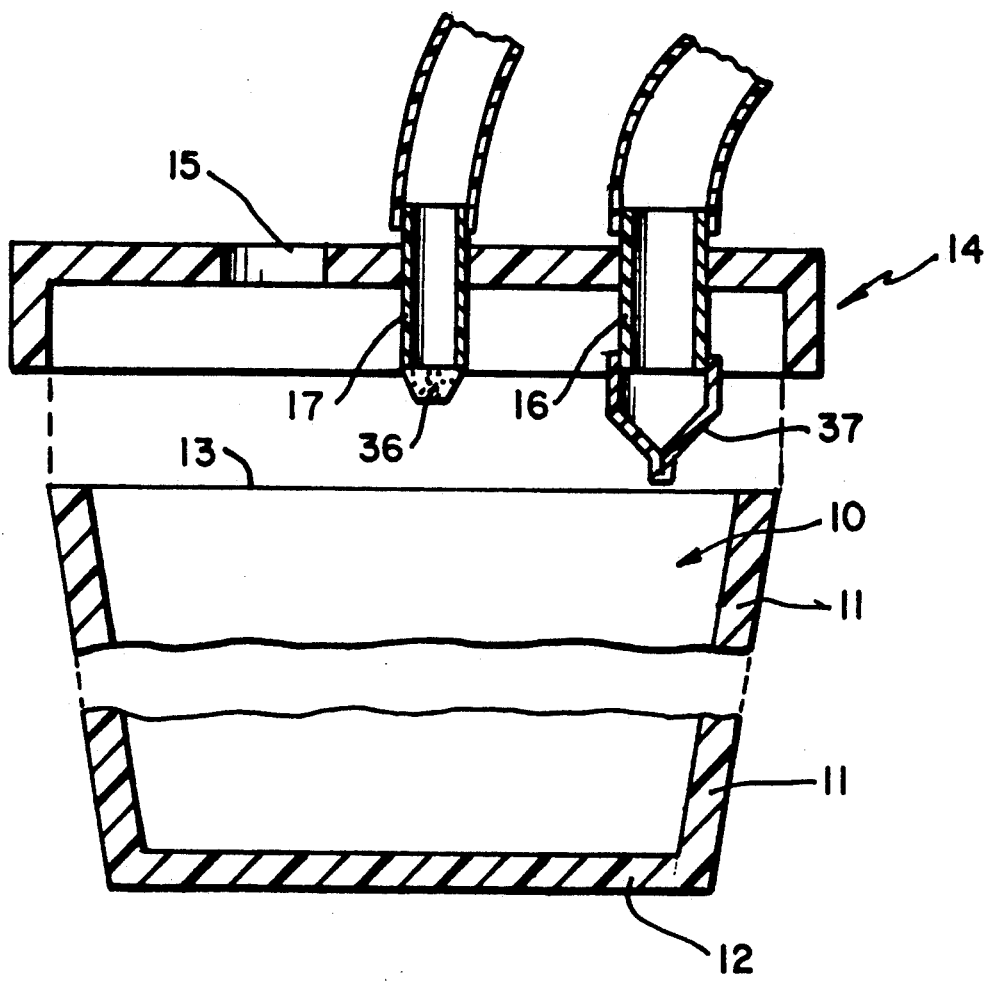
FIG. 1 is a cross-sectional view or a typical collection vessel shown broken away, to be used with any of the articles of the invention.

In accordance with the invention there is provided a composition to aid in the safe and convenient disposal of aqueous waste fluids by mixture of said composition therewith, whereby said fluids rendered non-flowable or immobile and/or disinfected.

Thus, one embodiment of the instant invention provides for a composition rendering aqueous waste fluids non-flowable and, if desired, disinfected with said composition comprising at least one hydrophilic xerogel comprising at least one water-insoluble hydrophilic polymer.

The water-insoluble hydrophilic polymers useful in accordance with the invention are those which are inherently water-insoluble and those which may be rendered so by crosslinking.

Examples of inherently water-insoluble hydrophilic polymers include copolymers of hydrophobic monomers, such as acrylonitrile, acrylates, (e.g., methyl and ethyl) methacrylates, (such as methyl and propyl) and styrene with hydrophilic monomers such as, acrylamide and acrylic and methacrylic acids and their salts and other polyelectrolytes, comprising pendant ionic groups, such as poly(vinyl sulfonic acid), poly(styrene sulfonic acid) and quaternary ammonium derivatives of, e.g., polystyrene and poly(2- or 4 vinyl pyridine). Other inherently water-insoluble hydrophilic polymers may be exemplified by hydrophobic polymers such as silicone, acrylate, methacrylate and urethane polymers whose surfaces have been rendered hydrophilic by treatments such as partial hydrolysis of e.g., ester and amide. groups and by grafting of hydrophilic monomers or other functional groups to the hydrophobic backbones, e.g., by plasma grafting of hydroxyl groups.

The inherently water-insoluble hydrophilic polymers useful in the practice of the instant invention include the acrylonitrile—acrylamide copolymers described in U.S. Pat. No. 4,331,784 and the modified acrylonitrile—acrylamide copolymers described in U.S. Pat. No. 4,337,327.

Other polymers of this nature include block copolymers of poly(ethylene oxide) and relatively hydrophobic materials such as polyurethanes which are described, e.g., by E. W. Merrill and E. W. Salzman in their article "Poly(ethylene oxide) as a Biomaterial" (Am. Soc. for Artificial Internal Organs Journal, April/June 1983, pp. 60–64). Such materials are exemplified by Polyox a crosslinked poly(ethylene oxide).

Water-soluble polymers which may be rendered insoluble by crosslinking include polymers of hydrophilic monomers such as those mentioned above, hydroxyalkyl acrylates and methacrylates and alkylene oxides such as those of ethylene and propylene. Such crosslinked hydrogels are described in, e.g., U.S. Pat. No. 3,323,960 and U.S. Pat. Re. No. 27,401.

Preferred insoluble hydrophilic polymers useful in the practice of the invention are the acrylonitrile-acrylamide (i.e., Hypan) and poly(ethylene oxide) copolymers as well as cellulose-starch-acrylates (such as Aquasorb).

Other materials which can function as xerogels include ground corn husks and the like.

Crosslinking may be effected by addition of crosslinking compositions, such as those which decompose into free radicals and polyfunctional materials; i.e. by exposure to radiation and by other means known to those skilled in the art.

Examples of compositions which decompose to form free radical are axonitriles, such as azobis (isobutyronitrile); peroxides, such as benzoyl peroxide; and hydroperoxides, such as cumene hydroperoxide.

Polyfunctional materials useful in crosslinking hydrophilic polymers include the acrylates and methacrylates of polyhydric compounds such as diols, e.g., ethylene glycol; triols, such as glycerol and 1,1,1-tris(hydroxymethyl) propane; tetraols, e.g., pentaerythritol and polyhydric polymers such as epoxy resins. Other crosslinking agents which may be used in the practice of the invention, as are well known in the art, include zinc oxide, organotin compounds, N,N'methylenebisacrylamide and diallylidene pentaerythritol.

Radiation-induced crosslinking may be effected by actinic radiation such as UV and visible light; radiation; and electron beams.

The resulting xerogels must, however, be such as will not react with the waste fluids to release undesirable products. Furthermore, said xerogels should not be reactive with other compositions, e.g. materials of construction, with which they may come in contact.

Therefore, in any particular case the xerogel composition will be chosen by the user in accordance with his requirements and the above considerations. Accordingly, every hydrophilic polymer cannot, necessarily, be used in all methods of practicing the invention.

In another aspect of the above embodiment the inventive compositions further comprise at least one disinfectant selected from the group comprising germicides such as bactericides, bacteriostats, fungicides, and the like.

Disinfectants which may be used in preparing the composition of the invention are known are to the art and include chlorine releasing compounds, such as Lysol, powdered bleach, iodine releasing compositions, e.g., idophors such as Providone, iodine; oxidants, such as benzoyl peroxide, alcohols such as ethanol; aldehydes and ketones such as glutaraldehydes and acetone; ionic and nonionic detergents including soaps, Non-idet and Triton, X-100; phenols such as o-phenylphenol (e.g Dowicide); mixed phenolic aldehydes such as p- and o-hydroxybenzaldehydes and 2,3- and 2,4- dihydroxybenzaldehydes; quaternary ammonium compounds such as octyl decyl dimethyl and dioctyl dimethyl ammonium chlorides and Dowicil; hexachlorophene, chlorohexidene gluconate; Germall; and the like, and appropriate precursors therefor and salts and mixtures thereof.

In that respect xerogels comprising pendant ionic groups such as the quaternary ammonium, phosphonato and sulfonato groups are both hydrophilic and disinfecting without the addition of other disinfecting components.

The compositions of the invention may be added to the waste fluids in the form of free-flowing powders, compacted tablets, and the like.

Thus, if the inventive composition were to be used for, say, disposal of spilled liquids the powdered form of the invention would be most practical. If, however, the composition is to be used to render fluids collected in a container non-flowable and, if desired, disinfected the form of said composition could, desirably, be a compacted form such a tablet, and the like, in order to decrease the rate of gelation.

The free-flowing powder forms of the compositions of the invention may further comprise non-reactive powdered carriers which may, if desired, also have absorptive capacity for the waste fluids. However, the absorptive capacity of said carriers may not be such that absorption of the waste fluids in said carriers and the invention composition would preclude gelation of the resultant mixture.

If the compositions of the invention are to be used in the form of compacted articles, e.g., as tablets, and the like, and cannot be compacted, per se. the components thereof are admixed with binders capable of being compacted. Such binding agents are well known in the art and will not be further discussed at this time. The binder materials may be reactive to the components of the waste fluid but not of the inventive composition.

The resultant mixtures are then prepared in the desired forms by methods known to the art. The compacted article must be such as will disintegrate upon contact with said waste fluids thereby releasing the composition of the invention to interact therewith.

However, it is desirable that the reaction of composition and waste fluids not be so rapid as to cause surface reaction on the articles before essentially complete mixing has been achieved. Such premature mixing might cause formation of a relatively impermeable crust on the inventive composition which could preclude effective mixing of the fluids and the composition whereby said fluids would not be rendered immobilized and, if desired, disinfected.

Therefore, it might be necessary to coat the composition with materials, i.e., encapsulate the components of the inventive composition within materials which will only gradually dissolve in the waste fluids thereby permitting essentially complete mixing before the major part of the interaction of waste fluid and composition occurs.

If desired, the active ingredients need not be mixed with carrier materials but might rather be encapsulated with compositions which will dissolve upon contact with the waste fluid, thereby releasing the active ingredients of the composition.

Furthermore, if desired, the compositions of the invention comprising binders whether in the form of free-flowing powder or compacted articles may also be so encapsulated.

Encapsulating compositions and methods of encapsulation are well known in the art and will not be further discussed at this time.

Thus, the article may be coated with a water-soluble composition which dissolves, slowly, on contact with the waste fluids, thereby permitting the inventive composition to be released for contact with the waste fluids, whereby they are rendered non-flowable and, if desired, disinfected.

As required, the disinfectant and xerogel components of the above compositions may be premixed and the mixture subsequently added to the collected fluids.

If the disinfectant component is in a liquid form it would be desirable to add the components of the composition to said fluids separately least the efficacy of the disinfectant be reduced by poor distribution thereof throughout the mixture.

Furthermore, it has been found that the effective concentrations of the components of some of the embodiments of the invention, when the liquid disinfectants are reactive with the xerogels, would be reduced.

Among such interactive components are the disinfectants comprising aldehyde groups (for instance, glutaraldehyde) and xerogels comprising amide (e.g., acrylamide) groups or disinfectants comprising iodine and xerogels comprising starch.

Under those circumstances, at least, it might be necessary to separate said components until just before addition thereof to the fluids. The foregoing problems might also be precluded by using solid derivatives of the disinfectants which would not be reactive with the xerogels and could be effectively distributed therethrough and where said derivatives could easily decompose upon contact with the waste fluids to yield the desired disinfectant.

Such derivatives include the bisulfite addition products of carbonyl group containing compounds, such as glutaraldehyde, which are easily decomposed, to form the carbonyl group containing composition, under the mildly acidic or alkaline conditions usually found in the collected fluids.

Precursors for the aldehyde-containing compounds for use in disinfecting acidic collected fluids also include the hemiacetals and acetals of said compounds.

If desired, acidic components, such as p-toluenesulfonic acid, or alkaline components, such as sodium carbonate, may be added to the inventive compositions, where the disinfectants are present in the form of such derivatives, to assure that the above conditions, for formation of the desired disinfectant, be present in the collected fluids.

However, it might still be necessary to effect such a separation, of the components of the composition of the invention, if it will be difficult for the disinfectant to get to all of the infectious agents which might be absorbed in the gel. Under those circumstances the disinfectant would first be permitted to interact with such agents and the thus treated fluids then immobilized by the xerogel.

The compacted articles may comprise varying relative quantities of the active (xerogel and disinfectant) ingredients and be of sizes which may vary in accordance with the needs of the user.

In the practice of the invention using any of the above embodiments the initial concentrations of the xerogel and disinfectant components would be determined by the absorptive capacity and disinfecting capability of the specific xerogel and disinfectant, respectively, being used. Although the compositions of the invention could be placed in the containers prior to entry of the waste fluids thereto, in order to interact with the waste fluids as they enter, they will, preferably, be made to contact such fluids just prior to removal of the collecting vessel from the patient in order not to interfere with sampling of the collected waste fluids.

The compositions, within such containers, may be made to contact the collected fluids, when desired, by opening the collection container and adding the compositions thereto in powdered or compacted form.

However, that would not be desirable as it might permit gaseous pathogens, within the container, to escape into the atmosphere of the fluids to spill from the container. Preferably, the compositions will be present in the container, from the beginning of the collection procedure, but separated from the fluids by a frangible or separable wall interposed therebetween until mixing of the fluids and inventive compositions is required.

When required, the wall is removed and the composition and the fluids permitted to mix and become non-flowable and, if desired, disinfected.

According to another embodiment of the invention there is provided a method of preparing aqueous waste fluids for convenient disposal, which comprises rendering said fluids immobile or non-flowable by treating said fluids with a composition comprising at least one hydrophilic xerogel comprising at least one water-insoluble hydrophilic polymer. In another aspect of said embodiment the inventive composition further comprises at least one disinfectant selected from the group of germicides, and germistats comprising bactericides and the like to render the treated gelled product non-infectious agents.

In yet another aspect of the above embodiment, when the waste fluids are spread over a surface the composition will be used in the form of a free-flowing powder which will be spread upon and admixed with said fluids, whereby the fluids will be absorbed by the composition to form a disinfected, non-flowable product which may be collected for safe disposal.

In another aspect of the above embodiment wherein the aqueous fluid waste materials have been collected in a disposable container the immobilizing comprising said xerogel and disinfectant composition is added to and mixed with said fluids, whereby the mixture is disinfected and caused to form a non-flowable, i.e., gelled, material.

In this aspect the composition may be used in the form of a free-flowing powder or an article comprising a compacted mass such as a table or "topedo" or suppository.

The powder or compacted article may be added to the container through its inlet port at any time prior to, during or after entry of the waste fluids.

However, it is preferable not to open the container once the waste fluids have started to enter therein least gaseous pathogens present therein escape therefrom into the atmosphere.

Thus, in a preferred aspect of this embodiment the composition of the invention is placed into the container before the waste fluids enter therein.

It is, nevertheless, necessary to prevent immediate mixing of the composition and fluids in order that the user be able to sample the fluids, if desired.

Therefore, the composition is placed in the container prior to use thereof but separated from the incoming fluids by a frangible barrier interposed therebetween.

The barrier may be used in the form of a burstable or pressure delaminable envelope, containing the composition of the invention, which is not reactive therewith or with the waste fluid materials.

In another aspect of this embodiment the composition may be contained in a compartment within said container and separated from the collecting compartment by a frangible wall wherein the walls of said compartment may be burst by methods known in the art, including a pointed rod entering said compartment from outside the container through a ring seal in the outside wall thereof.

In that aspect, when mixing of the composition of the invention and the fluids is desired the rod is forced through the wall of the compartment permitting the inventive composition to be discharged therefrom into the collecting chamber and mix with the waste fluids so as to render them non-flowable and disinfected.

In the event the waste fluids are accidentally permitted to spill onto an exposed external surface, then the inventive composition, usually in the form of a free-flowing powder, is sprinkled thereon and caused to mix therewith. The resultant product comprising a xerogel comprising said composition and the waste fluids is then collected, by known means, placed in proper receptacles and disposed of in accordance with the usual and customary procedures.

As a consequence of the interaction of the compositions of the invention and the waste fluids, the fluids are rendered immobile whereby their disposal is not messy and any infectious components thereof, if present are rendered harmless by the disinfectant and placed in condition form simple disposal by occlusion in the resultant xerogel.

According to a preferred embodiment of the invention a composition comprising a mixture of Aquasorb, 99.5 pbw (Aquasorb is the trademark of Guardian Chemical, Inc. a division of United-Guardian, Inc., Hauppauge, N.Y. for its cellulose-acrylate-starch xerogel) and 0.5 pbw of a quaternary ammonium compound is sprinkled upon a liquid spread upon a surface.

The liquid and said mixture immediately form a string-like gel which is collected and placed in a container for ultimate disposal in accordance with standard procedures.

In another preferred embodiment the above is repeated except that said immobilization composition is added to container containing waste fluids and at least one infectious agent.

The liquid is rendered immobile by forming a gel with said composition. In addition, the infectious agent is rendered inactive.

In a modification of the invention, as described above, where immobilization of the fluids is not required, the inventive compositions may be comprised of a least one disinfectant, as described above, and no xerogel component.

According to another aspect of the invention there is provided an article to be used for the addition of any of the compositions of the invention to a closed waste fluids collection vessel without opening said vessel after collection of said fluids has commenced.

Embodiments of the articles of the invention are illustrated by the Figures of the patent drawings wherein similar numbers identify similar parts.

FIG. 1 is a schematic illustration of a collection vessel, indicated by numeral 1, comprising a chamber 10 having a bottom wall 12, side walls 11 and a large top opening 13. The opening is closed by a cap 14, which may be sealed thereto, and comprises a port 15, and inlet means 16 so as to permit entrance of the fluids to the vessel and with outlet means 17, for application of a suction to the vessel.

Figure 2:
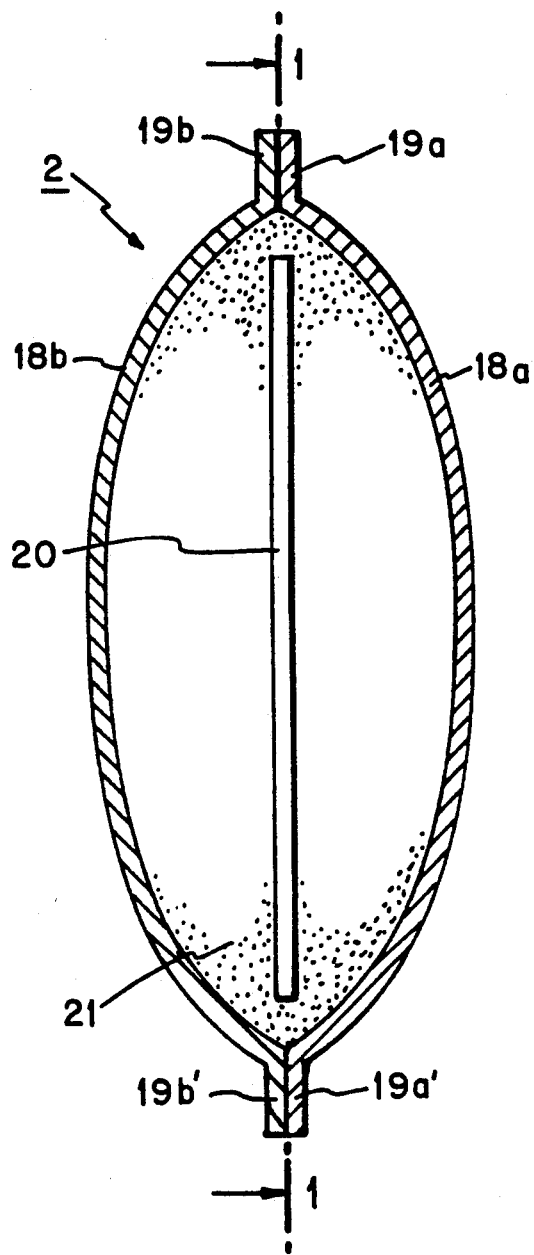
FIG. 2 is a cross-sectional view of an article made according to a first embodiment of the invention.
Figure 3:
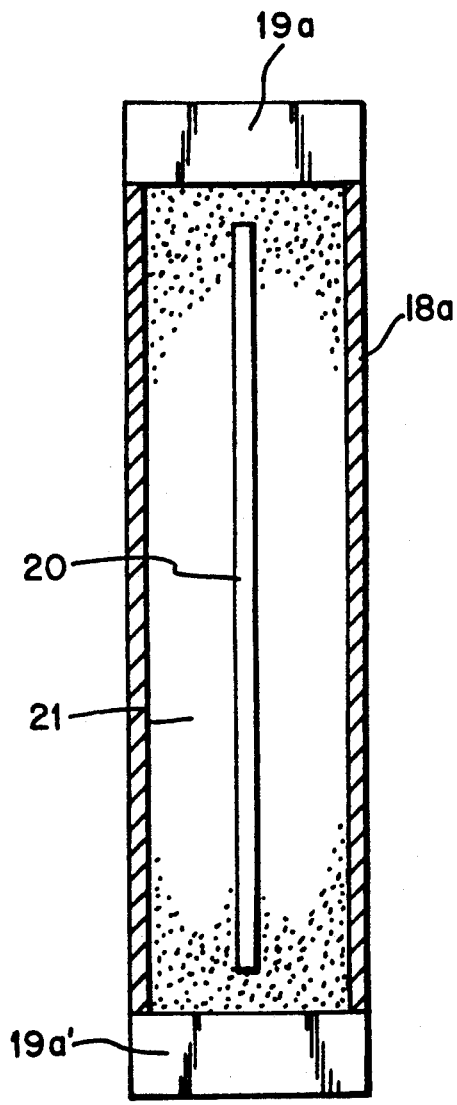
FIG. 3 is a sectional view of the article shown in FIG. 2, and taken along line 1—1 of FIG. 2.

In FIGS. 2 and 3, there is illustrated an article for the addition of the above-indicated inventive compositions to a collection vessel such as is illustrated in FIG. 1, comprising a flexible, hollow, collapsible envelope, indicated by numeral 2, comprising two flexible member 18a and 18b sealed to each other at first end portions 19a and 19b and opposite end portions 19a' and 19b' and at their side edges. The members encompass a chamber 21 to contain the compositions. The members 18a and 18b comprise materials which are soluble in, or attacked by said fluids so as to cause said articles to disintegrate upon contact therewith.

In the practice of using said article, it is filled with the desired composition and sealed. The article is then placed in the vessel which is sealed after which collection of the waste fluid commences. The walls of the article begin to disintegrate upon contact with the waste fluids and release their contents to admix with, and immobilize and, if desired, disinfect the waste fluids.

In connection with the above, the components of the composition, where said composition comprises a disinfectant, are premixed before being placed in said article.

If, however, the components are reactive with each other, e.g., where the disinfectant comprises a carbonyl group (such as glutaraldehyde) and the xerogel comprises an amide group (such as an acrylamide) it will be necessary to separate them at least until just before addition of the composition to the waste fluids.

FIGS. 4 through 6 illustrate an article, indicated by numeral 3, for use in connection with the above article whereby such separation may be effected.

The article comprises a housing comprising two semi-rigid members 22a and 22b in sealed contact with each other at their adjacent first ends 23a and 23b and their side edges. The housing, which is open at its other end encompasses a hollow, collapsible chamber 24.

The other ends 25a and 25b of the members 22a and 22b, respectively, are in sealed contact with each other at their sides, thereby providing a channel 27 from chamber 24 to a transverse opening 28.

The chamber 24 encompasses a sealed, burstable container, indicated by numeral 29, for the disinfectant. Such container comprises a sealed cavity 30 surrounded by end walls 31a and side walls 31b.

Figure 7:
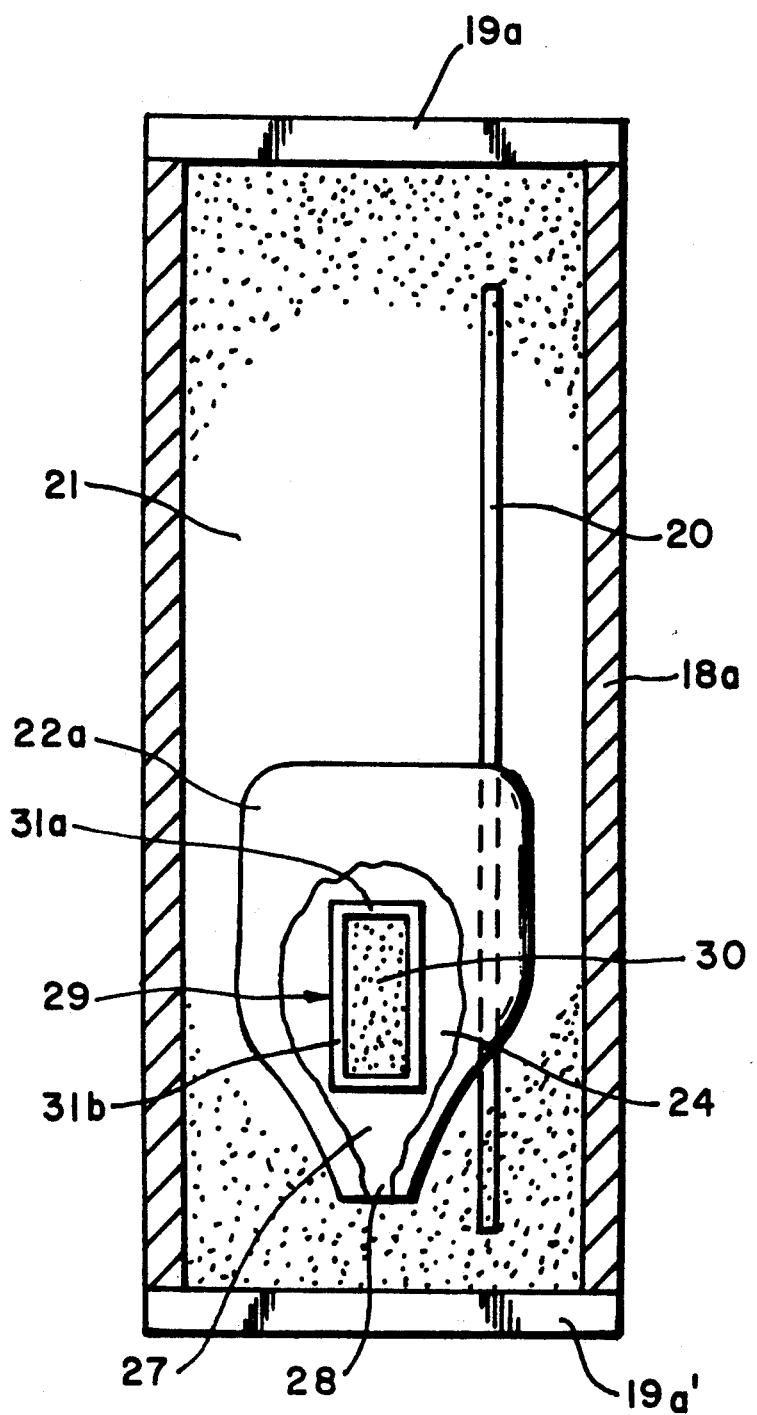
FIG. 7 is a side elevational view in section of a modification of the embodiment of FIG. 2.

In the practice of the invention, article 3 comprising the burstable container is emplaced, as shown in FIG. 7, in chamber 21 of the embodiment of FIGS. 2 and 3 and the walls of the article are sealed.

When it is desired to treat the waste fluids with the composition of the invention comprising the admixture of the disinfectant and xerogel components, the burstable container is broken by pressure, e.g., from fingers, thereon through walls 18a and 18b and 22a and 22b of article 2 and article 3, respectively, thus releasing its contents to the chamber 24 of article 3. The article 3 is then collapsed by additional pressure thereto and the composition forced through 27 to enter chamber 21 of article 2 through opening 28. The disinfectant and xerogel are then mixed, e.g., by shaking and such article containing the resultant composition is placed within a vessel for the collection of said waste fluids and the collection commenced.

As the article 2 disintegrates its contents are released into the fluids, whereby infectious agents therein are destroyed or, at least deactivated, by the disinfectant and the fluids immobilized by gelation of the xerogel.

If desired, in the use of any of the articles of the invention, the vessel is shaken during the collection of the waste fluids and after termination so as to facilitate mixing of the composition with said fluids.

After collection of the fluids has been terminated and the fluids immobilized and/or disinfected, the vessel is removed from the source of the fluids and the suction source and disposed by known means.

It is sometimes desirable to add the components of the composition, of the invention, to the vessel separately, e.g., where they are too reactive with each other to be mixed even just prior to addition to the vessel or where it is desired to disinfect the fluids prior to immobilization thereof.

It is sometimes found that the articles 2 through 3 buckle over and float at the top of the fluids, thus making their disintegration more difficult and slowing the release of their contents to the collection vessel.

It has been found that the problem may be avoided by providing means to maintain the articles in an extended condition at least until much of the disintegration has been effected.

Such means include providing reinforcement for the walls of the containers.

Another means, which is more cost-effective, is to insert a thin, rigid splintlike member, as illustrated in FIGS. 2 through 7, by elongated member 20 whose diameter, or width, usually about one-eighth ($\frac{1}{8}$) inch, is much less than that of the container and whose length is approximately that of the chamber 21. It is, of course, to be understood that the member 20 may not be comprised of materials which will react with the active components of the composition, prior to their interaction with the waste fluids, to avoid reduction of their effective components. Said member 20 may also if desired, consist of a coiled spring of similar dimensions. Also, if desired, the members 20 may be emplaced within a sealed sheath (not shown) to prevent interaction with the invention compositions.

In the use of the any of articles 2 through 3, the port 15 comprises means for sealing thereof after any of the articles 2 through 3 has been inserted into the vessel.

If desired, the outlet means 17 and inlet means 16 may be fitted with a one-way valves, 36 and 37, at their inlet and outlet ends, respectively, to prevent suction of the fluids into the outlet means or the escape of pathogens through the inlet means. Such valves 36 and 37 include, but are limited to, hydrophobic filters and butterfly valves, respectively.

In another aspect of the invention addition means 38 are inserted partially through the port 15 of the vessel and sealed to the cap 14.

Figure 8:
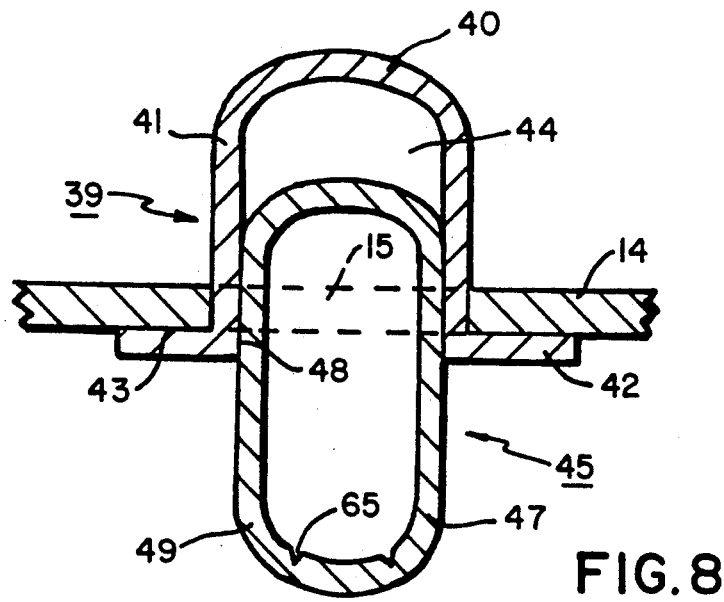
FIG. 8 is a fragmentary sectional view of another embodiment of the invention.

In one embodiment, illustrated in FIG. 8, of this aspect, means 38 comprises a housing 39, comprising an upper wall 40, situated above the plane of the cap 14, from which there descend side walls 41 terminating in a flange 42, extending normally outward therefrom and sealed to the underside of cap 14 at 43. The housing encompasses a chamber 44 open at its lower end. A sealed container 45, containing a composition of the invention is placed in the housing 39, a portion of whose outer side walls 47 are in adherent contact with a portion of the inner side walls 47 are in adherent contact with a portion of the inner side wall 41 of housing 39 at 48. The bottom wall 49 of the container 45 comprises a material which will disintegrate by contact with the waste fluids.

If desired, all of the walls of said container 45 may comprise said disintegrating material.

In using this embodiment the container 45 is filled with the inventive composition and sealed. It is then placed in chamber 44 of housing 39. Housing 39 is then placed in port 15 of cap 14, its upper wall 40 extending above the plane of cap 14 and its flange 42 being sealed to the underside of said cap at 43.

The cap is then sealed to the collection vessel by any means known to the art.

Collection of the fluids commences and the bottom wall 49 of the container 45, which is comprised of a material degradable by said fluids, disintegrates releasing its contents to mix and interact with said fluids.

After collection of the fluids has terminated, the vessel is removed from the fluids and vacuum source and it together with its treated fluids is disposed of by known means.

Figure 9:
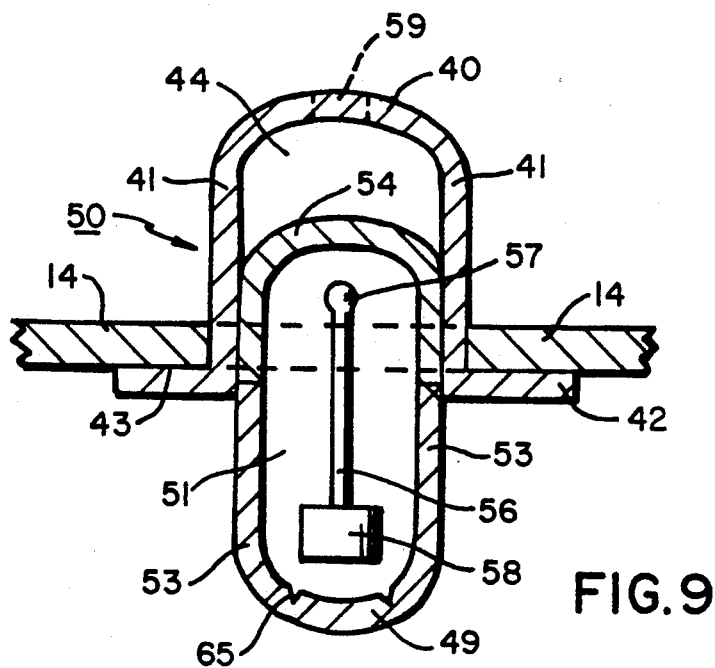
FIG. 9 is another fragmentary sectional view illustrating a modification of a portion of a further embodiment of FIG. 8.

In a modification of the above embodiment, illustrated by FIG. 9, the walls of the container 45 need not disintegrate by action of the fluids. In this embodiment, the container 45 is replaced by a container, indicated by numeral 50, which comprises plunger means 51 for separating a bottom portion 52, by applying pressure thereto, from the side walls 53 of said container. The upper wall and a upper portion of the side walls indicated by numerals 54 and 55, respectively, of the container 50 comprise a flexible, distortable material through which pressure may be applied to the top 57 of the plunger means described below.

The plunger means, examples of which are well known in the art, comprises a thin elongated member 56 which can receive pressure applied thereto, through means 57 at its top, whereby it is caused to descend thereby causing approximately horizontal means 58 at its lower end to push out a portion of the lower wall 52 of container 50, thereby permitting the composition contained therein to mix and interact with the contents of the vessel.

In this embodiment, a section 59 of the upper wall 40 of housing 39 comprises a flexible material which may be depressed by slight pressure thereon to apply pressure to the plunger means causing it to descend.

If desired, the upper portion housing 39 may be covered by a removable cap (not shown) to prevent premature depression of said section 59.

Figure 10:
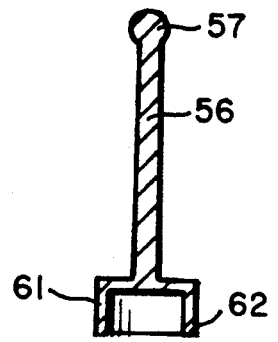
FIG. 10 is a further sectional view of a change to illustrating a modification of a part of the embodiment of FIG. 9.

FIG. 10 illustrates a modification of this embodiment in which the horizontal means 58 of the plunger is replaced by a hollow chamber, comprising a horizontal upper wall 60 sealed to the bottom of said trunk 45, and side walls 61 descending therefrom. The side walls terminate at beveled knife edges 62 which, when pressure is applied to the plunger through means 57, cut through the bottom wall 52 of container 50 so as to cause a portion thereof to be separated from the container whereby its contents are released to the vessel to act as indicated above.

If desired, the bottom walls 49 of the containers 45 may be prescored as at 65 to facilitate the separation of the bottom walls of the container 45.

Figure 11:
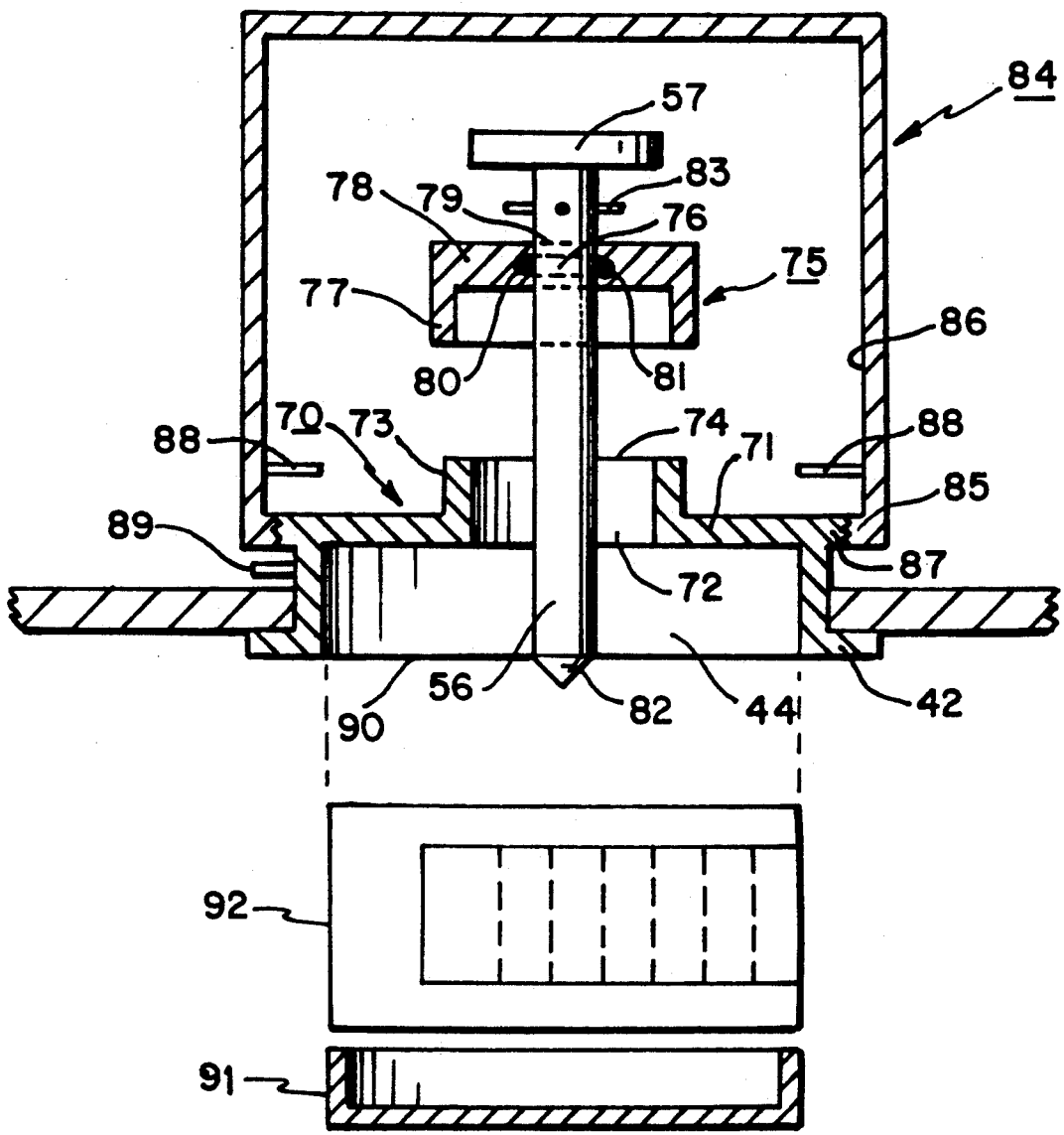
FIG. 11 is a sectional view of yet another embodiment of the article of the invention.

FIG. 11 illustrates another embodiment of the article of FIG. 8 comprising a housing 70, comprising an upper wall 71 situated above the plane of the cap 14, from which there descends side walls 41 terminating in a flange 42, extending normally outward therefrom and sealed to the underside of cap 14 at 43. The housing encompasses a chamber 44 comprising a large bottom opening to receive a sealed container containing a composition according to the invention. The upper wall 71 comprises a small opening 72 through which the lower portion of the elongated member 56 of the plunger means can pass.

A ring 73, rises normally upward from the edges of said opening and terminates in opening 74.

The opening 74 is encompassed by cap means 75 having a port 76 through which said member 56 can pass into the chamber 44.

If desired, the cap means may comprise a flexible, e.g., rubber tube comprising a bottom wall comprising a large bottom opening through which the side walls of said ring 73 may pass. The inner portion of the side walls 77 of the cap being in contact with and surrounding the outer portion of the side walls 73 of the ring, and an upper wall 78 comprising a small upper port 79 has a diameter slightly less than that of the elongated member 56.

In a modification of the above embodiment, the cap means may comprise a rigid cap, which may be attached to the housing 70 by known means, e.g., matching threaded portions on the inner and outer walls of the cap and housing, respectively, comprising a port 76, with the inner portion of the side walls of said port comprising a circumferential groove 80 for receiving a flexible O-ring 81.

The plunger means comprises an elongated member 56 comprising a flat, hemispherical or pointed portion 82. At its upper end the plunger is terminated by handle means 57. The elongated member of the plunger means is passed through opening 79 and port 76 into sealed contact with the walls of the opening of the above-indicated flexible tube 75 or the O-ring of the rigid cap 75. The elongated member may further comprise a plurality of break-away tabs 83 which will prevent inadvertent depression, under an accidentally applied slight pressure, of the plunger, but will break-away, under an intentionally applied greater pressure, to permit depression of the plunger into chamber 44.

It will often be desirable to provide means to cover the addition means of the invention to prevent accidental depression of the plunger means.

Such cover means, as known to the art, include cap means 84 which comprises a threaded portion 85, on its inner wall, to engage complementary outer threads 87 on the side wall of housing 70. Means are provided either on the cap 84, as at 88, protecting normally inwardly from the inner portion 86 of the side wall thereof, or on the housing 70, as at 89, projecting normally outwardly from the outer portion of the side wall 41 thereof, to prevent the cover from descending too low and depressing the plunger means.

In the use of this embodiment of the invention a sealed container 92, as described above, containing any of the above compositions of the invention is placed into chamber 44 the bottom opening 90 of which is sealed by an easily detachable cover 91.

When it is desired to have the composition of the invention, contained in said container to mix with the waste fluids, the cap means 84 is removed, pressure is applied to the handle 57 of the plunger means thereby causing it to descend into chamber 44.

Depending upon the position of said container 92 the plunger means will either press on the upper surface thereof causing it to descend and force the easily detachable cover 91 to separate from the flange 42, or the plunger means itself will force the cover 91 to detach, whereby the container will be caused to enter the chamber of the collection vessel to be contacted by the waste fluids and release its contents to mix with and immobilize and, if desired, disinfect said fluids.

In another embodiment of the invention, illustrated in FIGS. 12 and 13, comprising the container of FIGS. 2 and 3, the member 20 comprises a coiled spring. (Said spring may optionally be contained in a sealed sheath.)

In this embodiment the container 2, which has been prefilled with any of the compositions of the invention, is rolled from one end to the other, as indicated by arrow A, to form a coiled article under high tension. The coiled container is placed in chamber 44 of any of the addition means, described above, of FIGS. 8-9 and 11.

Figure 14:
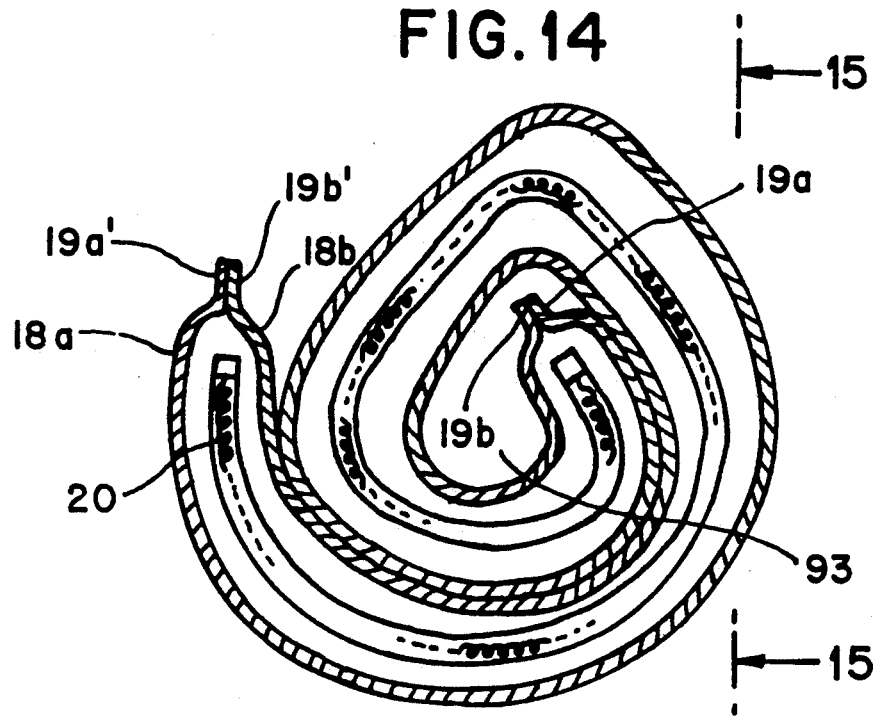
FIG. 14 is a further sectional view of the article of FIG. 12 completely rolled up for use in the practice of the invention.
Figure 15:
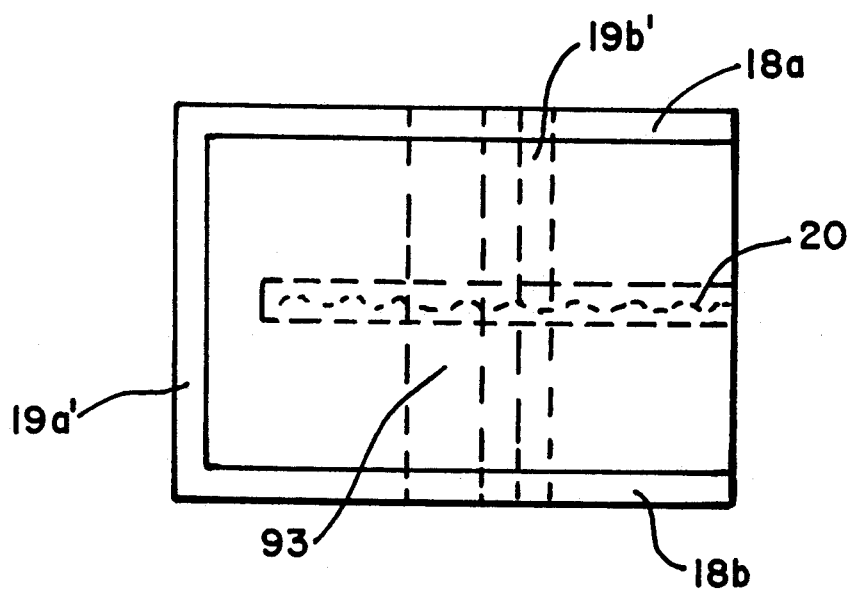
FIG. 15 is a view of the article of FIG. 14 taken along the line 17—17 of FIG. 14.

When mixing of the inventive compositions and the waste fluids is required, pressure is applied to the container if its surface is approximately normal to the face of the bottom portion 82 of the plunger means and therethrough to the cover 91, if present, of said chamber whereby the container is forced out of the addition means. If, however, the transverse axis of the container 92 is approximately parallel to the lengthwise axis of plunger stem 56, then the stem passes through the central hole 93, shown in FIG. 14, surrounded by the container 2. Upon exiting the chamber the container uncoils due to the tension from the contained spring, and becomes elongated thereby presenting a maximum surface for contact with the fluids within the collection vessel therewith.

After elongation, the container functions as described above with respect to the container of FIGS. 2 and 4.

In the event it is desired to add the components of the composition, to the vessel, separately, either where they are too reactive with each other or because disinfection is desired before immobilization is effected, two means such as those represented by FIGS. 8 through 14 may be utilized, in conjunction with two ports 15, wherein said means may be of the same type or different with the proviso that the means be utilized in a manner to effect addition of the disinfectant, to the waste materials, before addition of the xerogel.

It will be apparent to those skilled in the art that changes as to composition, form and arrangement of parts may be made without departing from the spirit of the invention.

What is claimed is:

1. A medical waste fluid kit for preparing for disposal waste fluid collected from a patient comprising:
    a substantially rigid, fixed shaped vessel having and being closed by a rigid cap having waste fluid inlet means for introducing a waste fluid into said vessel, and outlet means extending from and through said rigid cap;
    a composition comprising at least one hydrophilic xerogel in the form of a powder which includes at least one water-insoluble hydrophilic polymer for immobilizing the waste fluid;
    a container, having a surface area, containing said at least one hydrophilic xerogel for placement in said vessel for disposal of said waste fluid collected in said vessel, and the surface area of said container comprising a material which breaks up when brought into contact with the waste fluid for releasing the at least one hydrophilic xerogel into said vessel for admixing with the waste fluid, thereby immobilizing said solidifying same within said vessel and minimizing the hazards of handling said waste fluid which may be infectious.

2. An apparatus according to claim 1 wherein the container is smaller in size than said vessel so as to be positionable within the vessel.

3. An apparatus according to claim 2, further comprising means to maintain the container in a substantially lengthwise and upright position within the vessel.

4. An apparatus according to claim 3, wherein said means comprises an elongated rigid member in the container which has a length approximately equal to the length of the container.

5. An apparatus according to claim 3, wherein said means is not reactive with the composition.

6. An apparatus according to claim 4 wherein said rigid member is enclosed within a sealed sheath.

7. An apparatus according to claim 1, wherein said composition further comprises at least one disinfectant.

8. A medical waste fluid kit for preparing for disposal waste fluid collected from a patient comprising: a substantially rigid, fixed shaped vessel having and being closed by a rigid cap for containing waste fluid and having waste fluid inlet means and outlet means extending through and from said rigid cap;
    a composition comprising at least one hydrophilic xerogel in the form of a powder which includes at least one water insoluble hydrophilic polymer for immobilizing the waste fluid and a disinfectant,
    a first container, having a first container surface area containing said at least one hydrophilic xerogel for placement in said vessel for disposal of said waste fluid collected in said vessel and the;
    first container surface area of said first container comprising a material which breaks up when contacted with the waste fluid for releasing the composition into the vessel for admixing with the waste fluid for immobilizing said waste fluid, thereby solidifying same within said vessel and minimizing the hazards handling said waste fluid which may be infectious; and
    a second container for holding said disinfectant; said second container being smaller in size than said first container so as to be positionable within said first container, and having a second container surface area which is breakable when pressure is applied to the second container for releasing the disinfectant and premixing the disinfectant with said at least one hydrophilic xerogel.

9. An apparatus according to claim 8 wherein the first is smaller in size than said vessel so as to be positionable within the vessel.

10. An apparatus according to claim 9, further comprising means to maintain the first container in a substantially lengthwise and upright position within the vessel.

11. An apparatus according to claim 10, wherein said means comprises an elongated rigid member in the first container which has a length approximately equal to the length of the first container.

12. An apparatus according to claim 10, wherein said means is not reactive with the composition.

13. An apparatus according to claim 11, wherein said rigid member is enclosed within a sealed sheath.

14. An apparatus according to claim 8, wherein the composition further comprises at least one disinfectant.

15. Medical waste fluid kit for preparing for disposal waste fluid collected from a patient comprising: a substantially closed, rigid, fixed shaped vessel having and being closed by a rigid cap for containing collected waste fluid and having waste inlet and outlet means extending from said rigid cap;

- at least one hydrophilic xerogel in the form of a powder which includes at least one water-insoluble hydrophilic polymer;
- a disinfectant;
- a first container for holding the disinfectant and being positionable within said vessel and having means for releasing the disinfectant into the vessel for admixing with the waste fluid and disinfecting the waste fluid; and
- a second container for holding said at least one hydrophilic xerogel being placed in said vessel for disposal of said waste fluid collected in said vessel, said second container having a second container surface area for contacting the disinfected waste fluid entering directly via said waste inlet into said vessel, said second container surface area comprising a material which breaks up when brought into contact with said disinfected waste fluid for releasing said at least one hydrophilic xerogel into said vessel and for admixing with the disinfected waste fluid for immobilizing said waste fluid, thereby solidifying same within said vessel and minimizing the hazards of handling said waste fluid which may be infectious.

16. An apparatus according to claim 15, wherein said releasing means comprises a first container surface area for contacting the waste fluid in the vessel and comprising a material which breaks up at a rate faster than the rate at which the second container surface area breaks up when both surface areas are simultaneously brought into contact with the waste fluid.

17. An apparatus according to claim 15 wherein said releasing means comprises:

- a burstable container disposed within the second container for holding the disinfectant, and being burstable by pressure applied thereto;
- an opening provided in the second container; and
- a porous sheath covering the opening;
- whereby said burstable container bursts under pressure for releasing said disinfectant from the burstable container and entering the porous sheath so as to mix with the waste fluid before the first container surface area breaks up and before the hydrophilic xerogel is admixed with the waste fluid.

* * * * *